(12) United States Patent
Leriche et al.

(10) Patent No.: US 6,262,306 B1
(45) Date of Patent: Jul. 17, 2001

(54) MATERIALS WITH FERROMAGNETIC PROPERTIES COMPRISING ORGANIC MOLECULES WITH MAGNETIC PROPERTIES, AND METHODS FOR MAKING SAME

(75) Inventors: Christian Leriche, Trets; Alain Le Mehaute, Gif-sur-Yvette, both of (FR)

(73) Assignee: Gemplus, Gemenos (FR)

( * ) Notice: Subject to any disclaimer, the term of this patent is extended or adjusted under 35 U.S.C. 154(b) by 0 days.

(21) Appl. No.: 09/230,638

(22) PCT Filed: Jul. 23, 1997

(86) PCT No.: PCT/FR97/01381

§ 371 Date: Aug. 19, 1999

§ 102(e) Date: Aug. 19, 1999

(87) PCT Pub. No.: WO98/04519

PCT Pub. Date: Feb. 5, 1998

(30) Foreign Application Priority Data

Jul. 26, 1996 (FR) .................................... 96 09476

(51) Int. Cl.⁷ ................................................ C07C 249/00
(52) U.S. Cl. .......................................... 564/271; 564/248
(58) Field of Search ...................... 564/271, 248

(56) References Cited

U.S. PATENT DOCUMENTS

| 3,253,022 | 5/1966 | Lindner . |
| 3,929,404 | * 12/1975 | Kalopissis et al. ............ 8/10.1 |

FOREIGN PATENT DOCUMENTS

| 1254120 | 11/1967 | (DE) . |
| 1620055 | 5/1970 | (DE) . |
| 0512926 | 11/1992 | (EP) . |
| 0645414 | 3/1995 | (EP) . |
| 0680989 | 11/1995 | (EP) . |
| 2121101 | 8/1972 | (FR) . |
| 2234277 | 1/1975 | (FR) . |
| 2262022 | 9/1975 | (FR) . |
| 2262024 | 9/1975 | (FR) . |
| 2684677 | 6/1993 | (FR) . |

OTHER PUBLICATIONS

Bauer, P.B. et al. Studies in . . . Tetrahedron 530 #2 pp. 337–341, 1974.
Griffiths, J. et al "Cyclopentor . . . " Chem. Ind. (London) #9 pp. 379–380, 1974.
Database Xfire Justus Liebigs Ann Chem v. 5608(1934) pp. 144–157.
Atkinson, R.S. et al. Thermal Decomposition . . . J. Chem. Soc. Permin Trans–1, 74(23) pp. 2619–2622.
Suzaui, Y et al. Cycloaddition reactions . . . J. Chem. Soc., Chem Commun #14, pp. 837–838.
Coburn, et al. Picrylamino . . . J. Heterocyclic Chem. v 9(1972) pp. 1039–1044.
Smith, W.F. et al. "Quenching . . . " J. Am Chem. Soc. v. 97, #10 pp. 2764–2770, 1975.
Serve D. "Les proprietes . . . " Bull Soc. Chim. Fr. 76 (11–12 ptz) pp. 1993–1998, 1976.
Herustroeter, W.G. "Determination of . . . " J. Am. Chem. Soc. v97 #11 pp. 3090–3096, 1975.

* cited by examiner

*Primary Examiner*—Samuel Barts
(74) *Attorney, Agent, or Firm*—Roland Plottel (57) ABSTRACT

New molecules having the general formula A:N—B, where A:N— is .alpha.-substituted conjugated cyclic amine, with N being the N atom; and B is an .alpha.-substituted cyclic radical. These materials have ferromagnetic properties and may be use in a variety of fields and particularly in any electromagnetooptical or magnetoresistive system.

25 Claims, 5 Drawing Sheets

MATERIALS WITH FERROMAGNETIC PROPERTIES COMPRISING ORGANIC MOLECULES WITH MAGNETIC PROPERTIES, AND METHODS FOR MAKING SAME

The application is a 371 of PCT/FR97/01381 filed Jul. 23, 1997.

The present invention relates to materials with ferromagnetic properties containing organic molecules with magnetic properties and methods for manufacturing these.

The molecules making up the materials proposed by the invention have what are referred to as magnetic properties since they have a permanent magnetic moment which specifically enables them to align themselves in a magnetic field. The materials proposed by the invention containing such molecules are what are known as ferromagnetic because they exhibit spontaneous magnetisation in the absence of an external field, the permanent magnetic moments of the molecules with magnetic properties which they contain tending to be aligned parallel with one another within an organisation in the solid phase.

Certain organic materials are known to possess ferromagnetic properties. Such materials are described in the patent documents fled under references EP-A-0 512 926, FR-A-2 710 648 and FR-A-2 684 677. These are zwitterionic copolymers such as the polymer below, for example, made from aniline and naphthylamine sulphonic acid:

The ferromagnetism of this copolymer appears in the solid state only, when there is repeated twisting, stabilised by an acid-base interaction involving the sulphonate groups, along the length of the polymer chain and along a stack of aromatic rings.

Turning to the prior art cited above, one problem which the invention is intended to overcome is that of providing a material whose ferromagnetic properties, due to the presence of organic molecules with magnetic properties within said material, are not attributable to twisting in a polymer or oligomer chain stabilised by acid-base interactions.

The preliminary objective of the solution proposed by the invention is to provide a solid material with ferromagnetic properties, characterised in that it contains organic mol ecules with magnetic properties which satisfy the following general formula:

$$A=N-B$$

in which

A=N— is a cyclic imine with a substituted conjugated structure in the α position, N being the nitrogen atom; and

B— is a substituted cyclic radical in the α position.

A second objective of the invention is to propose a method of making a solid material with ferromagnetic properties such as defined above, characterised in that it includes a step whereby a B—NH$_2$ amine derivative of B— is mixed in a solvent with an O=A=B quinionic derivative of A=. By preference, the solvent is DMSO and the mixture contains a Lewis acid of the BF$_3$ type in stoichiometric quantities, mixing being effected at a temperature ranging between 80 and 200° C. and crystallisation taking place in a magnetic field.

The A=N—B molecule is not macro-molecular and does not constitute a polymer. It has, intrinsically, magnetic properties as well as organisation and correlation properties and, as a result, will lead to the production of a ferromagnetic material. This molecule is not stabilised by acid-base bonds involving positive and negative charges, particularly of the sulphonate groups.

A= is preferably a hydrocarbonic monocyclic or polycyclic unsaturated radical, possibly poly-substituted, each cycle comprising 3 to 15 carbon atoms and possibly being interrupted by one or more heteroatoms N, S or O.

More preferably, A= is a quinone, aminoquinone or cyclopentadienyl ring, substituted at the α, α' positions at least by substituents $Y_1$ and $Y_2$ and complying with the following formulas respectively:

-continued

Clearly, if A= is a polycylic radical such as a naphthoanthraquinone or fluorenyl radical, $Y_1$ and/or $Y_2$ will then correspond to a ring portion. This being the case, substituents satisfying the definition of $Y_1$ and/or $Y_2$ will then, advantageously, be present in the peri-positions of the polycyclic radical, for example, at the 1 and 7 positions in a naphthoquinone radical where the nitrogen atom is in position 8; or in positions 1 and 8 in an anthraquinone radical where the nitrogen atom is in position 9.

B— is preferably an unsaturated, hydrocarbonic, mono- or polycyclic, mono- or poly-substituted radical with a conjugated, possibly polysubstituted structure, each ring having 3 to 15 carbon atoms and possibly being interrupted by one or more heteroatoms N, S or O.

More preferably, B— is a benzene ring, substituted at least at positions α, α' by substituents $X_1$ and $X_2$ and complying with the following formula:

Clearly, if B— is a polycyclic radical such as a naphtho or anthracene radical, $X_1$ and/or $X_2$ will then correspond to a ring portion. This being the case, the substituents satisfying the definition of $X_1$ and/or $X_2$ will then, advantageously, be present at the peri-positions of the polycyclic radical as illustrated below:

In the molecules defined above for A=N— and B—, the substituents $R_i$ may be electron donors or acceptors and in particular will be substituents selected from among the radicals defined below for $X_1$, $X_2$, $Y_1$ or $Y_2$.

The molecules of the invention exhibit a more marked magnetic nature if the substituents of the cyclic radical of the imine are electron acceptors and if the substituents of the cyclic radical of B— are electron donors, i.e. if said substituents induce an electronic displacement of the cyclic radical B— towards the cyclic imine A=N— with a conjugated structure.

Consequently, in the molecules proposed by the invention, the substituents of positions α, α' of the cyclic radical B—, i.e. $X_1$ and $X_2$ in the above-mentioned formulas, are advantageously electron donors such as —$NH_2$, —NRH, —NRR, —OH, —OR, —R where —R is an alkyl, cycloalkyl, aryl, cycloalkylalkyl, arylalkyl radical and possibly includes one or more heteroatoms. In particular, $X_1$ and/or $X_2$ are selected from among the following radicals: —$NH_2$, —$NMe_2$, —OH, —OMe, and —iPr.

In addition, in said molecules, the substituents at positions α, α' of the A= ring conjugated with imine, i.e. $Y_1$ and/or $Y_2$ in the formulas given above, are, advantageously, electron acceptors such as —$NO_2$, —COR, —$CO_2R$, —COOR, —$SO_3R$, —$SO_2R$ where R is an alkyl, cycloalkyl, aryl, cycloalkylalkyl, arylalkyl radical and possibly includes one or more heteroatoms. In particular, $Y_1$, and/or $Y_2$ are selected from among the following radicals: —$NO_2$, —$SO_{3H}$, —$SO_2Me$, —$SO_3Me$, —$CO_2H$, —$CO_2Me$ and —COMe.

In the ground state, each molecule A=N—B is subject to constraints which are mainly steric in nature, imposed on them by the substituents which they carry at the α and α' positions of their cyclic radicals A= and B—. These substituents take up position on said molecule A=N—B at the level of the nitrogen atom and therefore cause orthogonalisation of the orbitals carrying the radical electrons, breaking the double bond A=N leads to the formation of a bi-radical A.—B. so that the electrons are then trapped on the rings and said molecules can then exhibit a spin correlation characteristic of the triplet state. Consequently, in the ground state, the molecules of the invention are generally in the triplet state, which is the source of the ferromagnetic properties of the materials proposed by the invention. Clearly, orthogonalisation is improved if the cyclic radicals are di-substituted at the α and α' positions, which increases the steric occupation at the level of the nitrogen atom. However, it should be pointed out that the A=N—B molecules which, in the ground state, are in the singlet state but whose energy needed for the changeover to the nearest triplet state is low, in the order of several kCal/mole, can easily change from the singlet state to the triplet state after a slight excitation, which may be magnetic, chemical, electrochemical or electric, for example, and will then be able bring about a crystallisation based on materials with ferromagnetic properties.

In a material such as proposed by the invention, n molecules are structured in the solid state in such a way that the said material exhibits ferromagnetic properties. n is a whole number greater than or equal to 1. n is selected so that it represents the rate of condensation in the solid state. This condensation is likely to take place, in spatial terms, along a single axis, (A=N—B)$_n$, so that a chain will be formed, or along several axes. In a first example, condensation of the n molecules in the solid state will take place by molecular stacking along a first axis, on which the cyclic radicals with a conjugated structure A= are superposed and the cyclic radicals B— are superposed and, in a second example, the condensation of the n molecules in the solid state takes place by molecular stacking on an axis along which the cyclic radicals with a conjugated structure A= are superposed on the cyclic radicals B—. In a third example, the molecules are stacked in the following manner:

If the molecules proposed by the invention do not need to be joined by covalent bonds in the crystallised solid state, there is particular advantage to be had if, in said solid state, the molecules are arranged in an ordered manner, for example stacked one on top of the other. It is for this reason that the method proposed as a means of manufacturing the materials of the invention incorporates the crystallisation step. However, the molecules of the invention may be grafted along a non-ferromagnetic polymer or may be copolymerised with one or more monomers or oligomers. Distributed regularly along a polymer chain, these molecules will then form a material exhibiting significant ferromagnetic properties.

Other features and advantages of the invention will become clear from the description of examples below, given by-way of illustration and not restrictive in any respect, with reference to the appended drawings, in which.

EXAMPLE 1

Several hundreds of molecules were examined in order to ascertain which of them were in triplet state in their ground state. These molecules are conducive to producing ferromagnetic materials, which themselves exhibit a triplet state.

For each of the molecules examined, the relative energy of the triplet state was calculated as compared with the singlet state. This energy, noted $E_{rel}$ and expressed in eV, is negative if, in the ground state, a molecule is in a triplet state. It is positive if, in the ground state, said molecule is in a singlet state. Only a small number of molecules amongst all the molecules examined satisfied this criterion. These were molecules of types I to VI, in which $X_1$, $X_2$, $Y_1$ and $Y_2$ are the substituents listed in the tables below.

| Type | I | I | I | I | I | I | I | I |
|---|---|---|---|---|---|---|---|---|
| $X_1$ | $SO_3H$ | $SO_3H$ | $SO_2Me$ | $NO_2$ | $NO_2$ | $CO_2H$ | $CO_2H$ | $CO_2Me$ |
| $X_2$ | $SO_3H$ | $SO_3H$ | $SO_2Me$ | $NO_2$ | $NO_2$ | $CO_2H$ | $CO_2H$ | $CO_2Me$ |
| $Y_1$ | $NH_2$ | $NMe_2$ | $NH_2$ | $NH_2$ | $NMe_2$ | $NH_2$ | $NMe_2$ | $NH_2$ |
| $Y_2$ | $NH_2$ | $NMe_2$ | $NH_2$ | $NH_2$ | $NMe_2$ | $NH_2$ | $NMe_2$ | $NH_2$ |
| $E_{rel}$ | −0.96 | −0.75 | −0.72 | −0.68 | −0.62 | −0.54 | −0.42 | −0.53 |
| (5, 4, 3, 2) | 44 | 16 | 38 | 10 | 4 | 10 | 2 | 10 |
| (4, 3, 2, 1) | −114 | −109 | −111 | −97 | −95 | 93 | −90 | −93 |
| (4, 3) | 1.312 | 1.307 | 1.312 | 1.314 | 1.306 | 1.311 | 1.305 | 1.311 |
| (3, 2) | 1.355 | 1.350 | 1.367 | 1.373 | 1.350 | 1.386 | 1.372 | 1.388 |
| (4, 3, 2) | 135.5 | 141.7 | 133.1 | 129.1 | 139.3 | 127.4 | 133.5 | 127.0 |

-continued

| Type | I | I | II | II | II | II | II | II |
|---|---|---|---|---|---|---|---|---|
| $X_1$ | $CO_2Me$ | $NH_2$ | $SO_2Me$ | $SO_2Me$ | $SO_3H$ | $SO_3H$ | $NO_2$ | $NO_2$ |
| $X_2$ | $CO_2Me$ | $NH_2$ | $SO_2Me$ | $SO_2Me$ | $SO_3H$ | $SO_3H$ | $NO_2$ | $NO_2$ |
| $Y_1$ | $NMe_2$ | $NH_2$ | $NH_2$ | $NMe_2$ | $NH_2$ | $NMe_2$ | $NMe_2$ | $NH_2$ |
| $Y_2$ | $NMe_2$ | $NH_2$ | $NH_2$ | $NMe_2$ | $NH_2$ | $NMe_2$ | $NMe_2$ | $NH_2$ |
| $E_{rel}$ | −0.43 | −0.50 | −0.80 | −0.81 | −0.86 | −0.80 | −0.82 | −0.63 |
| (5, 4, 3, 2) | 1 | 2 | −92 | −82 | −104 | −99 | −158 | −166 |
| (4, 3, 2, 1) | −89 | −88 | 0 | −11 | 19 | 2 | 46 | 34 |
| (4, 3) | 1.305 | 1.316 | 1.321 | 1.324 | 1.319 | 1.327 | 1.323 | 1.318 |
| (3, 2) | 1.373 | 1.412 | 1.315 | 1.317 | 1.322 | 1.325 | 1.361 | 1.350 |
| (4, 3, 2) | 133.6 | 121.8 | 139.5 | 139.7 | 141.4 | 138.7 | 129.6 | 131.8 |

| Type | II | II | III | III | III | III | III | III |
|---|---|---|---|---|---|---|---|---|
| $X_1$ | $CO_2H$ | $CO_2H$ | $NH_2$ | $NH_2$ | $SO_3H$ | $COOH$ | $SO_3H$ | $NO_2$ |
| $X_2$ | $CO_2H$ | $CO_2H$ | $NH_2$ | $NH_2$ | $SO_3H$ | $COOH$ | $SO_3H$ | $NO_2$ |
| $Y_1$ | $NH_2$ | $NMe_2$ | $COOH$ | $NO_2$ | $NH_2$ | $NH_2$ | $NMe_2$ | $NH_2$ |
| $Y_2$ | $NH_2$ | $NMe_2$ | $COOH$ | $NO_2$ | $NH_2$ | $NH_2$ | $NMe_2$ | $NH_2$ |
| $E_{rel}$ | −0.58 | −0.36 | −0.02 | −0.02 | −0.13 | −0.50 | −0.03 | −0.29 |
| (5, 4, 3, 2) | −175 | — | 85 | 83 | 23 | 17 | 51 | 15 |
| (4, 3, 2, 1) | 86 | — | −1 | 2 | 13 | 34 | 14 | 23 |
| (4, 3) | 1.315 | — | 1.333 | 1.319 | 1.344 | 1.323 | 1.391 | 1.323 |
| (3, 2) | 1.394 | — | 1.290 | 1.293 | 1.316 | 1.352 | 1.306 | 1.335 |
| (4, 3, 2) | 125.5 | — | 140.3 | 143.6 | 130.3 | 131.5 | 123.3 | 133.3 |

| Type | III | IV | IV | IV | V | V | VI |
|---|---|---|---|---|---|---|---|
| $X_1$ | $CO_2H$ | $SO_3H$ | $SO_3H$ | $NO_2$ | $NH_2$ | $NH_2$ | $NH_2$ |
| $X_2$ | $CO_2H$ | $SO_3H$ | $SO_3H$ | $NO_2$ | $NH_2$ | $NH_2$ | $NH_2$ |
| $Y_1$ | $NMe_2$ | $NH_2$ | $NMe_2$ | $NMe_2$ | $COOH$ | $NO_2$ | $SO_3H$ |
| $Y_2$ | $NMe_2$ | $NH_2$ | $NMe_2$ | $NMe_2$ | $COOH$ | $NO_2$ | $SO_3H$ |
| $E_{rel}$ | −0.40 | −1.03 | −0.93 | −0.64 | −0.02 | −0.02 | −0.05 |
| (5, 4, 3, 2) | −2 | 45 | 43 | 8 | 85 | 83 | −73 |
| (4, 3, 2, 1) | 90 | −115 | −135 | −91 | −1 | 2 | 145 |
| (4, 3) | 1.310 | 1.308 | 1.308 | 1.305 | 1.333 | 1.319 | 1.342 |
| (3, 2) | 1.389 | 1.354 | 1.338 | 1.367 | 1.290 | 1.293 | 1.328 |
| (4, 3, 2) | 129.4 | 135.9 | 141.1 | 133.2 | 140.3 | 143.6 | 138.3 |

In these tables, (5,4,3,2) represents the dihedral angle ($C_5,C_4,N_3,C_2$) expressed in degrees, (4,3,2,1) represents the dihedral angle ($C_4,N_3,C_2,C_1$) expressed in degrees, (4,3) represents the distance ($C_4,N_3$) expressed in Å, (4,3,2) represents the angle ($C_4,N_3,C_2$) expressed in degrees and (3,2) represents the distance ($N_3,C_2$) expressed in Å. The values of (5,4,3,2) and (4,3,2,1) provide information about the relative situation of the two cyclic nuclei and (4,3,2) provides evidence of the constraints, particularly steric constraints, which are exerted on the nitrogen atom.

From the tables above, it can be deduced that the molecules which are in the triplet state in their ground state exhibit an angle (4,3,2) ranging between approximately 120° and approximately 145°, which varies from 123.3 to 143.6 and on average is equal to approximately 130°. The orbitals carried by the molecules are therefore quasi-orthogonal.

These tables also demonstrate that the substituents $X_1$, $X_2$, $Y_1$, $Y_2$ act not only on the basis of their capacity as donor or acceptor electrons but also by dint of the steric occupation which they cause on the nitrogen atom. Consequently, the energy $E_{rel}$ is lower if $X_1=X_2=$—$NH_2$ than if $X_1=X_2=$—$NMe_2$ even though —$NH_2$ is not as good an electron donor as —$NMe_2$, —$NH_2$ certainly providing a better compromise in terms of the steric occupation which it brings to the nitrogen atom.

Clearly, the relative energy calculated for the triplet state also applies to the molecules in the gaseous state. In the solid state, these results may be modified.

EXAMPLE 2

Different ways of synthesising the materials proposed by the invention have been devised. In this example, 250 mg (1.49 mmole) of 2,3,5,6-tetraaminobenzoquinone and 600 mg (3.39 mmole) of 2,6-diisopropylaniline were mixed in 6.5 ml of DMSO (dimethylsulphoxide) in a 100 ml dual-necked flask under agitation. 1 ml of $BF_3$, $Et_2O$ was then-added slowly and the mixture obtained was heated to 140° C. for 12 hours. Then, having ceased the agitation, the mixture was left to cool slowly to ambient temperature. Several hours later, the mixture was filtered on sinter N° 4 and a solid material, black in colour, was obtained which was washed several times in ethanol and dried under vacuum. This material, obtained by the reaction depicted below, should contain a mixture of molecules I and II as follows:

MOLECULE I     MOLECULE II

However, it is possible that said material will also contain molecules having more than two rings, in particular three, or are the dimers of molecules I and II.

12.5 mg of this material were then placed on a Faraday balance which shows a magnetic force whose value is 17.36 compared with 1380 for the same mass of powdered nickel. It is therefore ferromagnetic. Knowing that nickel has a magnetisation of 40 electromagnetic units (emu)/g at saturation, it can be deduced that the synthesised product has a magnetisation close to 0.5 emu/g.

The addition of increasingly higher quantities of $BF_3$ to the reaction medium does not produce higher quantities of ferromagnetic product. Moreover, the next two tests, conducted under the synthesis conditions outlined above for this example, show that an increase in the quantity of $BF_3$ reduces the ferromagnetic nature of the materials of the invention.

| Test | Quantity of $BF_3$ (ml) | Magnetic force per 12.5 mg of product |
|---|---|---|
| 1 | 1.0 | 17.36 |
| 2 | 3.0 | 0.85 |

Figure 1A:
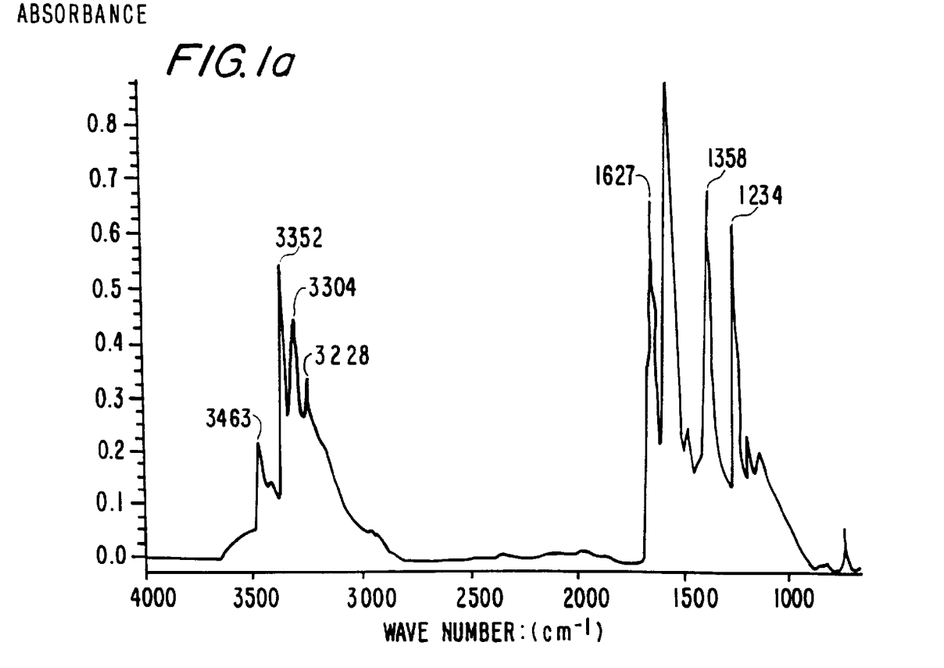
FIGS. 1A and 1B show the IR spectra of materials proposed by the invention crystallised under the various operating conditions defined in an example 2.
Figure 1B:
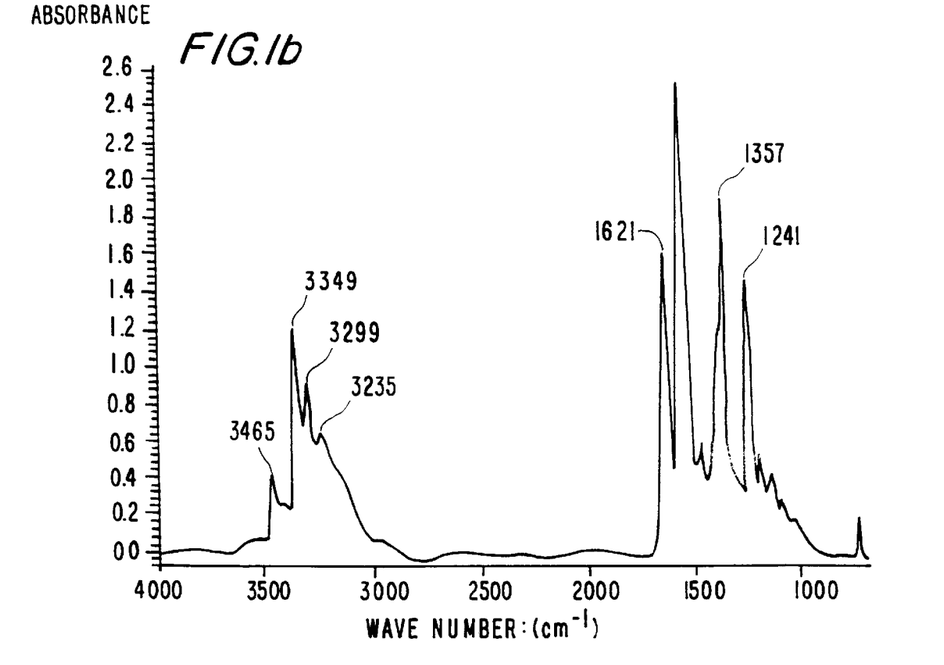

However, as illustrated in FIGS. 1A and 1B, the IR spectra of test products 1 and 2 are similar.

Figure 2A:
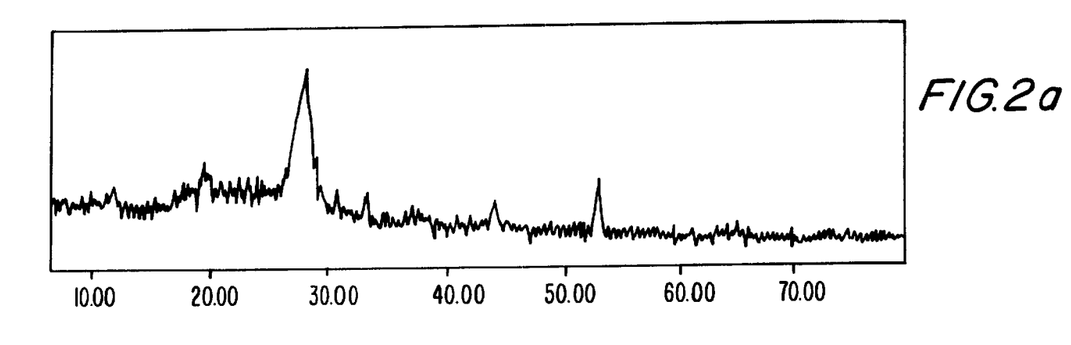
FIGS. 2A and 2B illustrate the XR spectra for the materials of example 2.
Figure 2B:
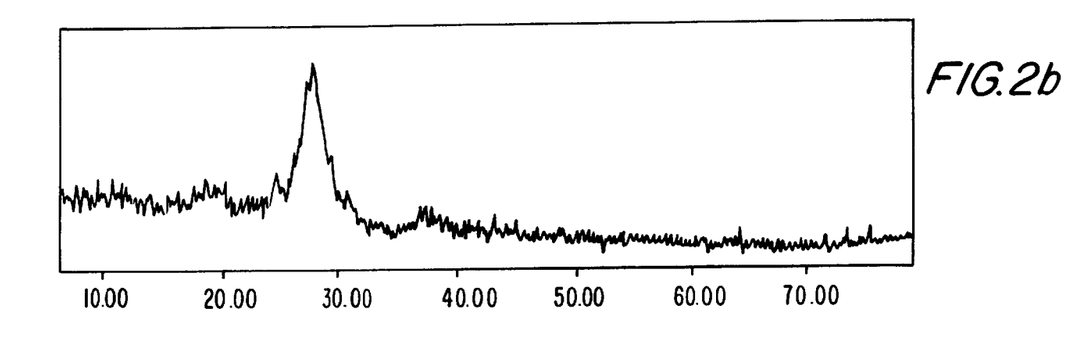

Consequently, it would seem that a same substance exhibits ferromagnetic properties or not according to the conditions of crystallisation imposed on it. However, as illustrated in FIG. 2A, the peaks of the XR spectrum of the substance of the first test, which relate to the substance whose ferromagnetic properties are marked, are better defined and finer than the peaks relating to the substance of the second test. The ferromagnetic substance is of the first test is therefore of a higher molecular order than that of the second test.

It would appear that there is particular advantage to be had from crystallising the molecules of the invention in DMSO in terms of producing substances with marked ferromagnetic properties.

In order to demonstrate the importance of crystallisation as a means of obtaining substances with marked ferromagnetic properties, the compound of the second test was made soluble in DMSO at temperatures in the order of 140° C. for 12 hours and the mixture was then left to cool to ambient temperature. The reading of the magnetic force for this substance on a Faraday balance showed that magnetisation is modified upwards.

To the same end, the reaction mixture was filtered, in a first test, and the filtrate obtained was washed with ethanol. During an initial period in a second test, the DMSO was evaporated off from said mixture producing a black oil and dichloromethane was then added to this, allowing a product to precipitate during a second period, which was then recovered by filtration.

| Test | Process | Magnetic force per 31.6 mg of product |
|---|---|---|
| 1 | filtration | 22.94 |
| 2 | evaporation | 0.37 |

It can be seen that magnetisation depends on the precipitation process. It can therefore be affirmed that magnetisation is clearly attributable to the organic chains and the order in solid phase.

EXAMPLE 3

500 g of 2,3,5,6-tetraaminobenzoquinone were dissolved in 8 ml of DMSO in the presence of 1 ml of etherate $BF_3$ and the mixture obtained was heated to 136° C. for 12 hours. Contrary to expectations, the black product obtained is not ferromagnetic, even though the infrared spectrum of the compound is similar to that of the ferromagnetic substance.

Other syntheses conducted in the presence of DMSO and in the presence of etherate $BF_3$ at 136° C. and for 12 hours were unable to produce the ferromagnetic substances of the invention. For example, the reactions with tetraphenylcyclopentadienone did not produce the expected results, whether it be with diisopropylaniline or trimethylaniline, given that in both cases a product was obtained which showed no change from the initial product.

EXAMPLE 4

In this example, the substance of example 2 with marked ferromagnetic properties was firstly tested in NMR. As a result of this test, it was noted that the resonance signals of the nuclei are highly disrupted by the internal field.

Figure 3:
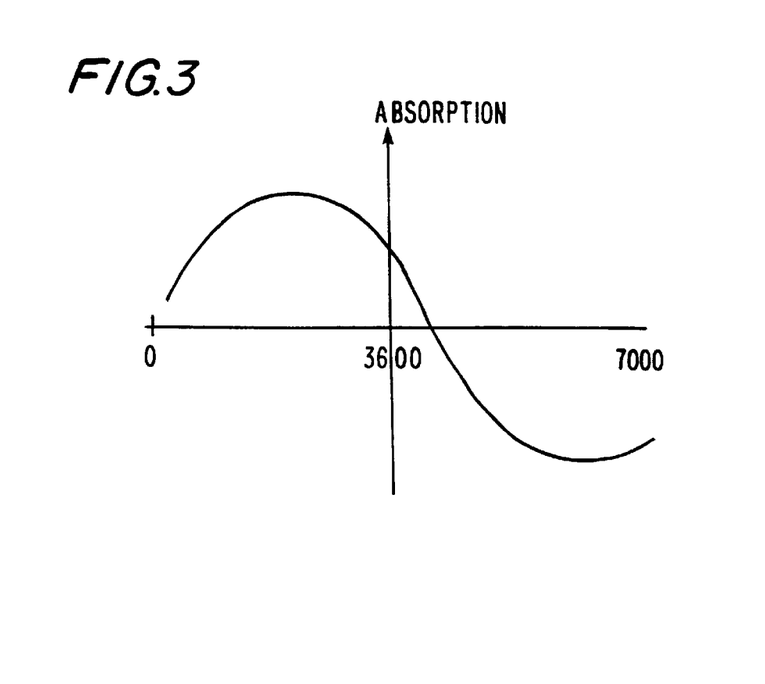
FIG. 3 represents the absorption signal obtained using electronic spectroscopy MFR for a material proposed by the invention.

This material was then tested under electronic spectroscopy MFR. The signal obtained, illustrated in FIG. 3, is a sinusoidal signal with widened resonance extending between 0 and 7000 Gauss, which corresponds to a ferromagnetic or ferrimagnetic substance with a high correlation between the spins.

Figure 4:
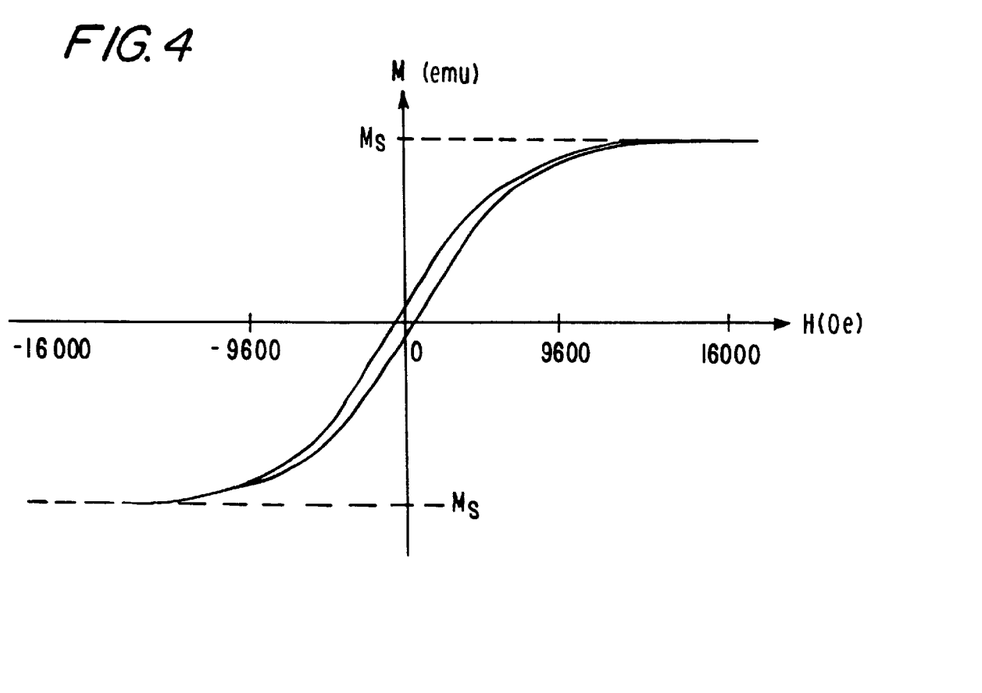
FIG. 4 represents the variation in magnetisation of a material proposed by the invention as a function of the magnetic field applied to it.

Finally, a last test conducted in a magnetometer with an alternating field gradient enabled an absolute measurement to be taken of the magnetisation of the substance at a temperature of 300 K. By measuring the variation of the magnetic signal M as a function of the cyclic variation of the field H, the curve illustrated in figure was obtained, in which the magnetic field H, expressed in Oersted (Oe), was plotted on the abscissa and the magnetic signal M or magnetisation, in emu, on the ordinate. This curve is characteristic of a ferromagnetic compound. It shows that the magnetisation of the substance at saturation is close to 0.5 emu/g to within about 1%, that is approximately ¹⁄₁₀₀ iron oxide. The maximum magnetisation is reached to within 10% at 9,600 Oe and it is complete at 16,000 Oe. The coercive field is therefore low and hysteresis zero or almost zero, less than or equal to 100 Oe.

The three tests in this example therefore confirm that the substance of the invention possess ferromagnetic properties and has a high correlation between the spins in its solid phase.

EXAMPLE 5

A quantitative analysis was conducted on the substance with ferromagnetic properties from example 2 to ascertain the content of Fe, Ni and Co. All of the measurements indicate contents very largely below 100 ppm, which confirms that the level of magnetisation observed is of organic origin.

EXAMPLE 6

The substance with marked ferromagnetic properties from example 2 was placed in the presence of metacresol vapour known as a means of secondary doping, in particular for the polyalinines, which enhances their conductivity. This doping reduces the magnetisation of ferromagnetic compounds with a base of aniline and naphthalene amino sulphonic acid. The magnetisation disappears in the presence of such vapours, which confirms the organic nature.

EXAMPLE 7

The substance with marked ferromagnetic properties from example 2 is dissolved in DMSO and then recrystallised by means of dichloromethane in a magnetic field of 2 teslas generated by an electromagnet. Whilst the substance has a magnetisation of 0.5 emu/g in its initial state, magnetisation rises to 5 emu/g after crystallisation.

EXAMPLE 8

In order to verify the thermal stability of the substances of the invention with ferromagnetic properties, differential thermal analyses (DTA) and thermal gravimetric analyses (TGA) were conducted on the substances obtained from tests 1 and 2 of example 2, dried under vacuum. The results of these analyses are set out respectively in FIGS. 5A and 5B, in which the scale on the abscissa represents the temperature in degrees Celsius and the scale on the ordinates on the left-hand side represent the loss of weight TG as a % and the scale of ordinates on the right-hand side represents the differential temperature DTA.

Figure 5A:
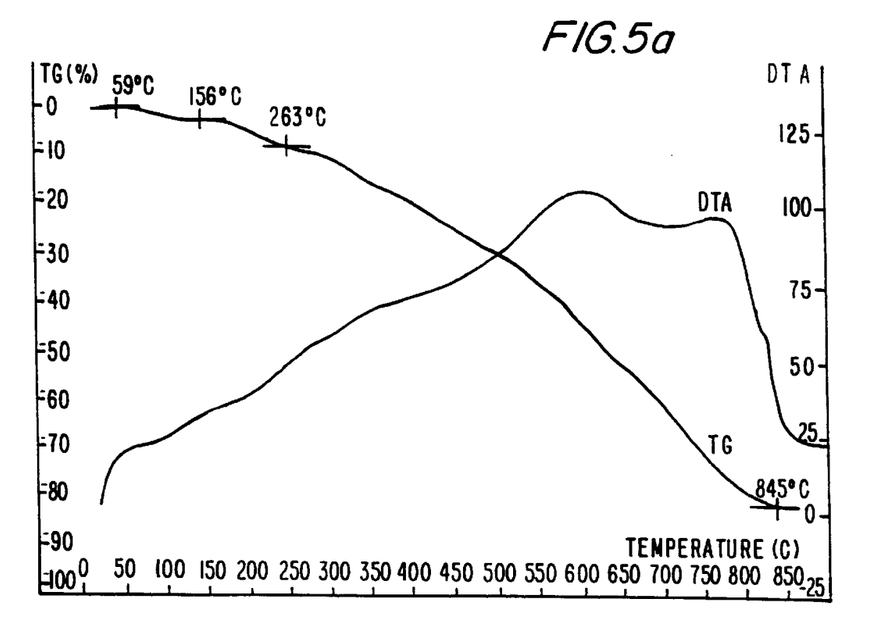
FIGS. 5A and 5B set out the test results of differential thermal analysis/thermal gravimetric analysis obtained on materials proposed by the invention.
Figure 5B:
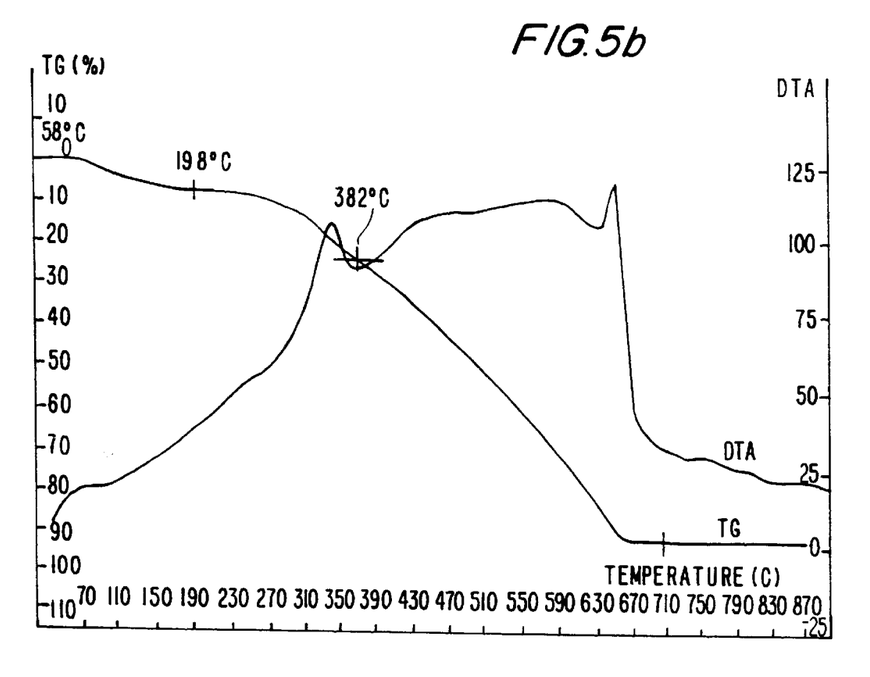

The results of these tests show that the substances of the invention have a remarkable thermal stability in air since it is possible to heat them to temperatures up to 200° C. without their ferromagnetic properties being affected.

EXAMPLE 9

The substance with marked ferromagnetic properties from example 2 was placed in a metallic wire coil. The magnetic field generated inside the coil was found to be altered as a result.

EXAMPLE 10

Figure 6:
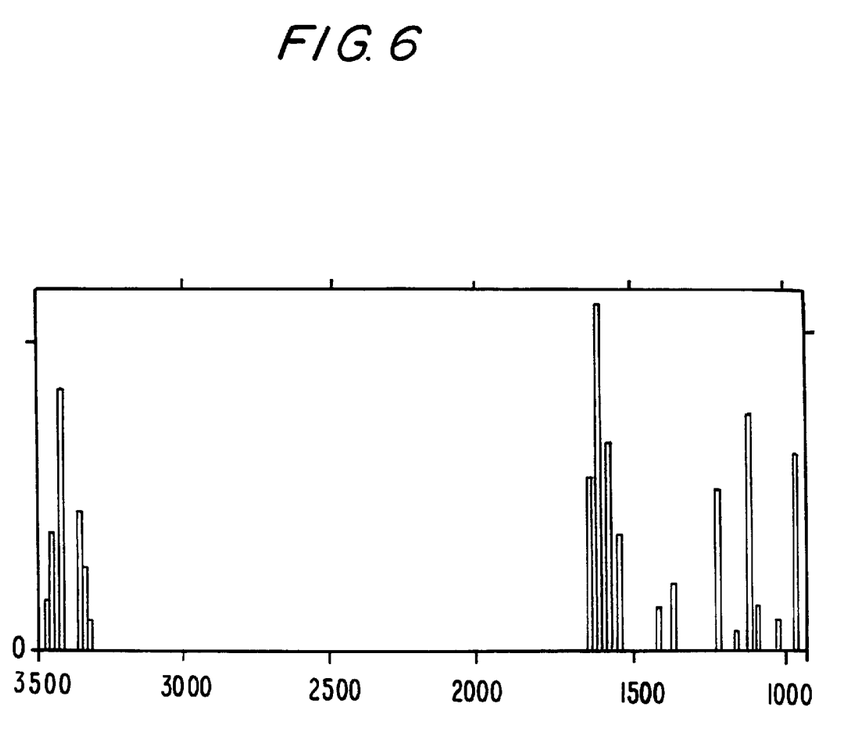
FIG. 6 shows a spectrum calculated from a fragment of a molecule of a material proposed by the invention.

In order to confirm the infrared spectroscopy results set out in FIGS. 1A and 1B, ab initio calculations were performed in which the spectrum of the molecule fragment below was modified:

This calculated spectrum is defined by the reference values in the tables below, in which a represents absorbance and n.o. corresponds to the wave number in $CM^1$.

| | | | | | |
|---|---|---|---|---|---|
| a. | 0.0977 | 0.1025 | 0.1082 | 0.1244 | 0.1324 |
| n.o. | 502.2 | 526.7 | 556.3 | 639.5 | 680.8 |
| a. | 0.1361 | 0.1398 | 0.1420 | 0.1511 | 0.1544 |
| n.o. | 699.7 | 718.4 | 729.9 | 776.7 | 793.6 |
| a. | 0.1613 | 0.1652 | 0.1685 | 0.1852 | 0.1952 |
| n.o. | 829.2 | 849.4 | 865.9 | 952.2 | 1003.3 |
| a. | 0.1981 | 0.2114 | 0.2166 | 0.2265 | 0.2292 |
| n.o. | 1018.1 | 1086.6 | 1113.5 | 1164.3 | 1178.2 |
| a. | 0.2387 | 0.2667 | 0.2750 | 0.2921 | 0.2954 |
| n.o. | 1226.8 | 1371.0 | 1413.7 | 1501.7 | 1518.3 |
| a. | 0.2997 | 0.3051 | 0.3056 | 0.3116 | 0.3134 |
| n.o. | 1540.6 | 1568.6 | 1571.1 | 1601.8 | 1610.8 |
| a. | 0.3192 | 0.6494 | 0.6512 | 0.6531 | 0.6534 |
| n.o. | 1641.0 | 3338.4 | 3347.4 | 3357.4 | 3358.7 |
| a. | 0.6653 | 0.6727 | 0.6732 | 0.6735 | 0.6750 |
| n.o. | 3420.0 | 3457.9 | 3460.6 | 3462.3 | 3470.0 |

The modelled spectrum of the above-mentioned molecular fragment, illustrated in FIG. 6, superimposes well on the IR spectra of FIGS. 1A and 1B, which confirms that the molecules of the materials proposed by the invention obtained in example 2 contain such a fragment.

The materials with ferromagnetic properties of the invention may be deposited in a thin layer, the thickness of which can be extremely low, in the nanometre range, on substrates such as polyethylene, polyvinyl chloride, methyl polymethacrylate, polycarbonates and epoxy resins. These thin layer deposits can be applied between layers whose properties are different. In particular, these layers are selected from among diamagnetic, ferromagnetic, ferrimagnetic and paramagnetic layers.

Furthermore, the magnetic properties of the materials proposed by the invention can also be adjusted. This adjustment can be made by chemical techniques using a catalytic structure, by electrochemical techniques, by mechanical methods using pressure, particularly with the aid of a piezoelectric material, or thermally.

Whether or not they are deposited in thin layers, the materials with ferromagnetic properties proposed by the invention lend themselves to applications in a large number of fields if their ferromagnetic properties are adjusted to suit the circumstances.

Examples of the uses to which the materials of the invention can be put are listed below, although this list is not intended to be restrictive. The applications in question cover fields involving hyperfrequencies, magnetic devices in general, electrical devices, data storage devices and photonics, the field of medicine and the manufacture of conductors or superconductors. In the field of hyperfrequencies, the materials of the invention would be suitable for use in ferrite phase shifters and ferritic antenna, circulators, isolators and electromagnetic screens, travelling-wave tubes and klystrons, inductance devices, delay lines and hyperfrequency chips. In the field of magnetic devices, the materials of the invention are likely to be used in magnetic tapes and cards as a substrate for magnetic bubble memories, in telephony devices such as sensors, actuators and amplifiers, in magnetic relays, in dampers and brakes, particularly eddy-current brakes, for the manufacture of magneto-rheological fluids, in compasses and in magnetic control and safety devices such as thermostats and gauges. In the field of electrical engineering, the materials of the invention are likely to be used in ferritic cores, levitation systems and bearings, write and erase heads, motors and contactless motors and transformers. In the field of data storage and photonics, the products of the invention are likely to be used in magneto-resistive memories, Hall effect memories, re-writable optical memories, magnetic and holographic imaging devices, phase shifters and convertors. Finally, in the field of medicine, the materials of the invention are likely to be used in imaging devices in nuclear medicine, in medicaments used for treating pathologies of viral and/or bacterial origin.

What is claimed is:

1. A solid material with ferromagnetic properties, characterised in that it has one or more organic molecules with magnetic properties, satisfying the following general formula A=N—B in which:

A=N— is a cyclic imine with a substituted conjugated structure at position α, N being the nitrogen atom; and B— is a substituted cyclic radical at site α.

2. A material as claimed in claim 1, characterised in that in the ground state, the molecule or molecules are in the triplet state.

3. A material as claimed in claim 1, characterised in that A= is an unsaturated, monocyclic or polycyclic hydrocarbonic radical, possibly polysubstituted, each ring having from 3 to 15 carbon atoms and possibly being interrupted by one or more heteroatoms N, S or O.

4. A material as claimed in claim 3, characterised in that A= is a quinone, aminoquinone or cyclopentadienyl ring substituted at site α'.

5. A material as claimed in claim 1, characterised in that B— is an unsaturated, monocyclic or polycyclic hydrocarbonic radical with a conjugated structure, possibly polysubstituted, each ring having from 3 to 15 carbon atoms and possibly being interrupted by one or more heteroatoms N, S or O.

6. A material as claimed in claim 5, characterised in that B— is a benzene ring substituted at site α'.

7. A material as claimed in claim 1, characterised in that the cyclic imine with a conjugated A=N— structure is substituted at site α by a substituent electron donor $Y_1$.

8. A material as claimed in claim 7, characterised in that the cyclic imine with a conjugated A=N— structure is substituted at site α' by a substituent electron acceptor $Y_2$.

9. A material as claimed in claim 1, characterised in that $Y_1$ and/or $Y_2$ are selected from among the following radicals: —$NO_2$, —COR, $CO_2R$, —CORR, —$SO_3R$, —$SO_2R$ where R is an alkyl, cycloalkyl, aryl, cycloalkylalkyl, arylalkyl radical and possibly has one or more heteroatoms.

10. A material as claimed in claim 9, characterised in that $Y_1$ and/or $Y_2$ are selected from among the following radicals: —$NO_2$, —$SO_3H$, —$SO_2Me$, —$CO_2H$, —$CO_2Me$ and —COMe.

11. A material as claimed claim 1, characterised in that the cyclic radical B— is substituted at site α by a substituent $X_1$ which is an electron donor.

12. A material as claimed in claim 11, characterised in that the cyclic radical B— is substituted at site α' by a substituent $X_2$ which is an electron donor.

13. A material as claimed in claim 1, characterised in that $X_1$ and/or $X_2$ are selected from among the following radicals: —X or X̄ is a halogen atom, —$NH_2$, —NRH, —NRR', —OH, —OR, —R where R is an alkyl, cycloalkyl, aryl, cycloalkylalkyl, arylalkyl radical and possibly has one or more heteroatoms.

14. A material as claimed in claim 13, characterised in that $X_1$ and/or $X_2$ are selected from among the following radicals: —$NH_2$, —$NMe_2$, —OH, —OMe, —Me and —iPr.

15. A material as claimed in claim 1, characterised in that it has one or more molecules satisfying one of the following formulas:

16. A solid material with ferromagnetic properties, characterised in that it has n molecules as claimed in claim 1, n being a whole number greater than or equal to 2 and in that the n molecules are condensed, the material satisfying the formula $(A=B—N)_n$ in which n is the rate of condensation.

17. A material as claimed in claim 16, characterised in that the n molecules are linked by covalent bonds.

18. A material as claimed in claim 1, characterised in that the molecules are grafted along a polymer.

19. A material as claimed in claim 1, characterised in that the molecules are copolymerised with one or more monomers or oligomers.

20. A method of manufacturing a material as claimed in claimed 1, characterised in that it includes a step whereby:

a B—NH$_2$ amine derivative of B— is mixed with a quinone derivative O=A=O of A= in a solvent.

21. A method as claimed in claim 20, characterised in that the solvent is DMSO.

22. A method as claimed in claim 20, characterised in that the mixture also contains an acid of the Lewis type BF$_3$.

23. A method as claimed in claim 22, characterised in that the Lewis acid is added in stoichiometric quantities.

24. A method as claimed in claim 20, characterised in that the mixing is conducted at a temperature ranging between 80 and 200° C.

25. A method as claimed in claim 20, characterised in that the material is crystallised in a magnetic field.

* * * * *